US007111589B1

(12) United States Patent
Terwilliger et al.

(10) Patent No.: US 7,111,589 B1
(45) Date of Patent: Sep. 26, 2006

(54) NOSTRIL SUPPORT DEVICE FOR HORSES AND OTHER ANIMALS

(76) Inventors: Al G. Terwilliger, 53 Massoit, Clawson, MI (US) 48017; Russell C. Norris, 1760 Primrose, Toledo, OH (US) 43613

( * ) Notice: Subject to any disclaimer, the term of this patent is extended or adjusted under 35 U.S.C. 154(b) by 0 days.

(21) Appl. No.: 10/189,787

(22) Filed: Jul. 3, 2002

Related U.S. Application Data

(60) Provisional application No. 60/302,738, filed on Jul. 3, 2001.

(51) Int. Cl.
*A61M 29/00* (2006.01)

(52) U.S. Cl. .......................................... 119/800; 606/199

(58) Field of Classification Search ................ 119/800; 54/80.3; 606/199
See application file for complete search history.

(56) References Cited

U.S. PATENT DOCUMENTS 1,014,758 A * 1/1912 Knowlson .................. 606/199
1,034,123 A * 7/1912 Knowlson .................. 606/199
1,232,956 A * 7/1917 Mooney .................. 606/199
2,672,138 A * 3/1954 Carlock .................. 606/199
5,464,413 A * 11/1995 Siska et al. .................. 606/151
6,004,342 A * 12/1999 Filis .................. 606/199
6,270,512 B1 * 8/2001 Rittmann .................. 606/199
6,540,766 B1 * 4/2003 Martino .................. 606/199

FOREIGN PATENT DOCUMENTS

GB 2 313 313 A * 11/1997

* cited by examiner

*Primary Examiner*—Peter M. Poon
*Assistant Examiner*—Susan C. Alimenti
(74) *Attorney, Agent, or Firm*—James M. Deimen

(57) ABSTRACT

A new nostril support device for a horse comprises a shaped body for insertion into the nostril and an integral clip that retains the body in position by pressing on the outside of the nostril. The shape of the body is generally convex toward the clip and concave away from the clip. In a direction substantially parallel to the clip the body is substantially straight at the bottom of the concavity. Overall the body tapers to a substantially parabolic edge to ease insertion into a nostril.

8 Claims, 1 Drawing Sheet

NOSTRIL SUPPORT DEVICE FOR HORSES AND OTHER ANIMALS

This application claims the benefit of provisional patent application No. 60/302,738, filed Jul. 3, 2001.

BACKGROUND OF THE INVENTION

The field of the invention pertains to devices to assist horses, in particular, race horses to breathe with less effort.

On some horses the nostrils tend to constrict, especially during high exertion in a race. Constriction of the nostrils results in decreased air flow and loss of breathing efficiency. Moreover, the loss of breathing efficiency puts stress on the horses lungs which can result in lung injury such as Exercise Induced Pulmonary Hemorrhaging (EIPH).

Horses with collapsed nostrils or extra flesh over the false nostril may have blocked airways. The horses may close down and stop at the end of a mile, for example, due to lack of oxygen and stress. Horses expend tremendous energy and effort to breathe during racing and other events. Thus, anything that inhibits breathing will have a deleterious effect on a horse that is strenuously exercising.

U.S. Pat. No. 5,913,873 discloses a spring loaded strip attached over a horse's nasal passages and held in place by a special adhesive. The strip lifts or stints the vestibular walls of the nasal passages.

SUMMARY OF THE INVENTION

The new nostril support device comprises a shaped body for insertion into the nostril and an integral clip that retains the body in position by pressing on the outside of the nostril. The shape of the body is generally convex toward the clip and concave away from the clip. In a direction substantially parallel to the clip the body is substantially straight at the bottom of the concavity. Overall the body tapers to a substantially parabolic edge to ease insertion into a nostril. Although the invention is not limited to the shape herein disclosed, this shape has been developed through extensive experimentation and testing to develop a shape comfortable for a horse thus leading to better and easier breathing by the horse during racing.

The nostril support is intended mainly for use on horses with collapsed nostrils or extra flesh over the false nostril that may block the airway and cause stress from a deprivation of oxygen. The nostril support spans the nostril cavity acting as a bridge which holds the nostril open. The false nostril is prevented from collapsing into the nasal passage and blocking the air flow. The nostril support allows the nostril to flair and contract normally without blocking or restricting air flow.

DESCRIPTION OF THE PREFERRED EMBODIMENT

Figure 1:
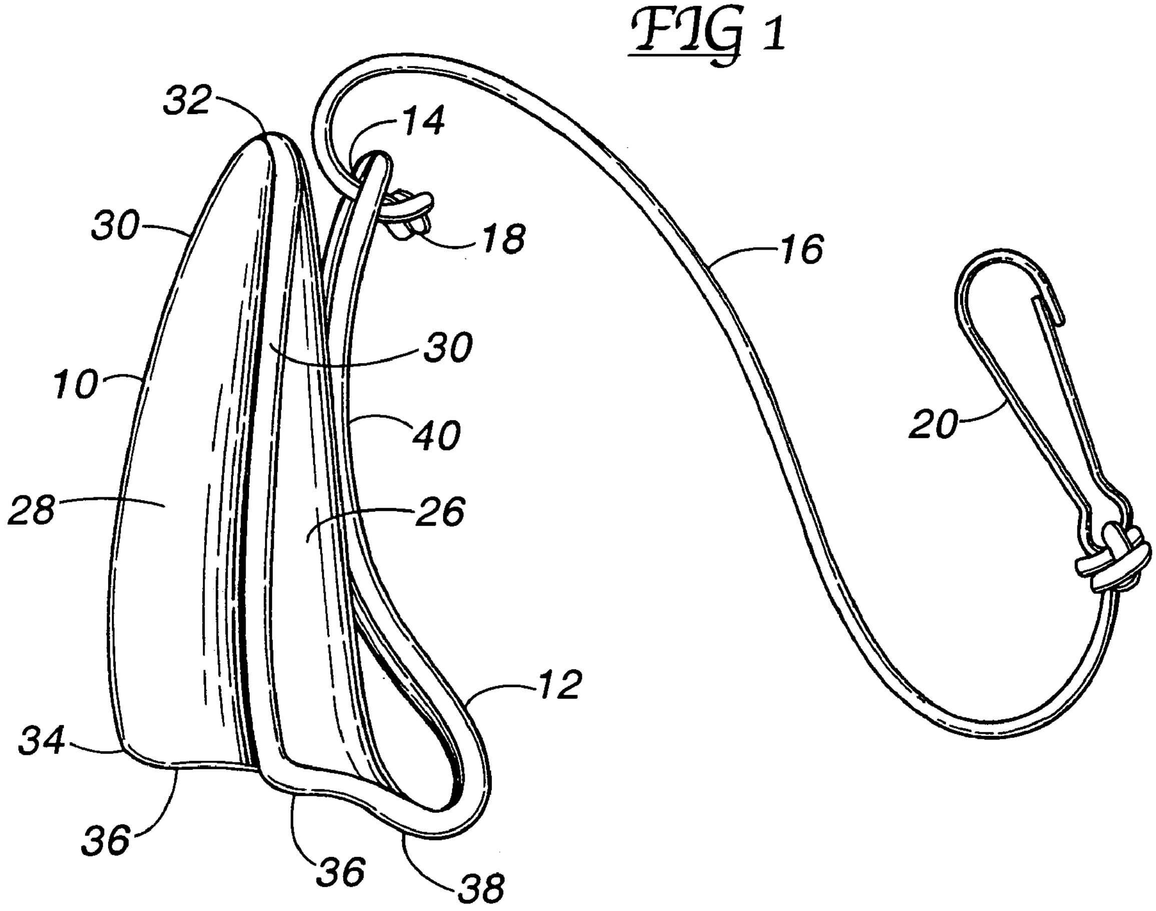
FIG. 1 is a perspective vew of the nostril support.

As illustrated in FIG. 1, the nostril support comprises a shaped body 10 and an integral clip 12. The clip 12 has a hole 14 for a cord 16 knotted at 18 to retain the cord to the clip. The cord 16 extends to a metal clip 20. The metal clip

Figure 2:
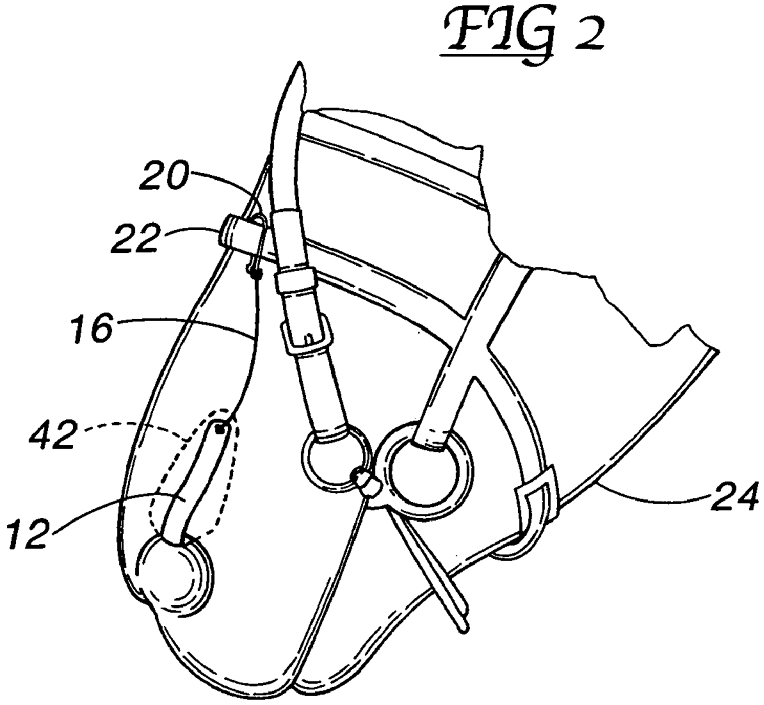
FIG. 2 is a perspective view of the nostril support as used on a horse.

20 is attached as convenient to the race halter 22 of the horse 24 as best shown in FIG. 2. Thus, the cord 16 prevents loss of the nostril support in the event that it is expelled from the horse's nostril.

The nostril support shaped body 10 is convex on the outside 26 toward the integral clip 12 and concave on the opposite side 28. The edges 30 of the body 10 generally form a parabola toward the tip 32 and smoothly flow toward the opposite end 34 where the body abruptly ends 36 and is integrally joined 38 to the clip 12. The clip 12 in turn is curved 40 toward the body to assist in retaining the clip to the nostril. The integral clip 12 and shaped body 10 are preferably formed from substantially rigid plastic, but may be made of other materials.

In FIG. 2 the nostril support is shown as used on a horse 24. The shaped body 10 is essentially within the nostril as shown in dotted outline 42 with the integral clip 12 outside. The shaped body 10 has been found to effectively prevent the nostril outside flesh from collapsing into the nostril during hard breathing by the horse such as during a race. The particular shape as described above and shown has been found through extensive testing to be very comfortable for the horse. In general, a pair of the nostril supports are used on the horse.

What is claimed is:

1. A large animal nostril support comprising a non-tubular single shaped for insertion into a single nostril and an external clip, the clip extending from an abrupt end of the body and alongside the body to engage and press against the exterior of the nostril immediately opposite the shaped body, the opposite end of the body smoothly substantially parabolically curved to aid insertion into the nostril, the smooth curvature extending substantially to the abrupt end of the body wherein the abrupt end is substantially perpendicular to the longitudinal axis of the body.

2. The nostril support of claim 1 wherein the body is concave in a direction away from the clip and convex toward the clip.

3. The nostril support of claim 1 including means to attach the clip to a race harness.

4. The nostril support of claim 1 wherein the body is substantially straight in a direction parallel to the clip, and convex transverse and toward the clip.

5. The nostril support of claim 4 wherein the abrupt end of the body terminates with the clip integrally extending therefrom.

6. The nostril support of claim 5 wherein the clip curves toward the body for engagement with the exterior of the nostril.

7. The nostril support of claim 5 wherein the edges of the body form the parabolic curve at the opposite end of the body.

8. A method of retaining a single nostril of a large animal open comprising inserting into the nostril a single non-tubular shaped body having a convex exterior, a concave interior and a substantially parabolically curved edge extending from an abrupt end of the body to the opposite end of the body to aid insertion into the nostril, and retaining the shaped body in the nostril with an external clip alongside the body engaging and pressing against the nostril exterior immediately opposite the shaped body wherein the abrupt end is substantially perpendicular to the longitudinal axis of the body.

* * * * *